(12) United States Patent
Kranbuehl

(10) Patent No.: US 7,069,772 B2
(45) Date of Patent: Jul. 4, 2006

(54) METHOD TO PREDICT THE END-POINT, REPLACEMENT TIME AND TO MONITOR CHANGES IN THAT TIME BY USING PRE AGED WITNESS COUPONS

(76) Inventor: David E. Kranbuehl, 201 Harrison Ave., Williamsburg, VA (US) 23186

( * ) Notice: Subject to any disclaimer, the term of this patent is extended or adjusted under 35 U.S.C. 154(b) by 176 days.

(21) Appl. No.: 10/840,272

(22) Filed: May 7, 2004

(65) Prior Publication Data

US 2005/0247103 A1 Nov. 10, 2005

(51) Int. Cl.
*G01N 3/00* (2006.01)
(52) U.S. Cl. .......................................................... 73/86
(58) Field of Classification Search .................... 73/86, 73/865.6
See application file for complete search history.

(56) References Cited

U.S. PATENT DOCUMENTS 5,614,683 A * 3/1997 Kranbuehl ................... 73/866
6,131,443 A * 10/2000 Duncan ......................... 73/86

* cited by examiner

*Primary Examiner*—Robert Raevis
(74) *Attorney, Agent, or Firm*—Whitham, Curtis, Christofferson & Cook, PC

(57) ABSTRACT

A method involving the use and creation of pre-aged witness coupons which characterizes and monitors the rate and extent of chemical and physical aging of the polymer in the structure during use in the field is described.

22 Claims, 3 Drawing Sheets

Polymer Liner from Retrieved Pipe

Pre-aged Coupon Cut from Pipe

Composite Coupon Holder

Figure 1:
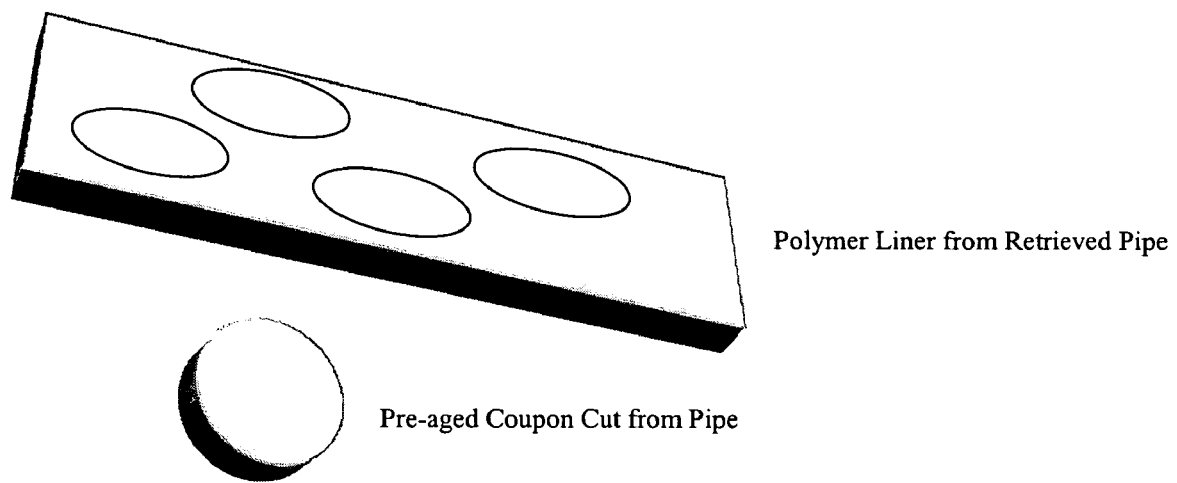

METHOD TO PREDICT THE END-POINT, REPLACEMENT TIME AND TO MONITOR CHANGES IN THAT TIME BY USING PRE AGED WITNESS COUPONS

FIELD OF THE INVENTION

This invention pertains to a method to determine in advance the time when material has aged to a point where the polymer component should be replaced. A particular example is polyamide (PA) liners as well as other plastics such as poly vinyl difluoride (PVDF) and polyethylene (PE) as well as its crosslinked form (PEX) used as the barrier liner in pipes used to transport oil and/or gas. But the method applies to any structure or component made from a polymer and where a pre-aged witness coupon is able to provide information in advance and more quickly on the rate of aging and the properties of the final state of degradation

DESCRIPTION OF THE PRIOR ART

Polymers are used to make many structures from airplane wings, to bridges to liners of tanks and pipes, all of which can result in catastrophic failure if degradation leads to a change below the needed strength and performance properties.

As an example polyamide (PA) materials and other polymers such as PVDF, PE and PEX are used as liners for a gas-oil-water barrier in pipes used to transport gas, oil, water and mixtures thereof. Materials such as PA-11, PVDF and PEX can age due to either chemical or physical-fatigue aging. The normal practice in the industry is to extrude a sheath in the shape of a continuous tube of a thickness ranging from several millimeters to several centimeters. This tube will be the principal barrier containing the fluid under flow. Sometimes a sacrificial layer several millimeters thick is extruded as a layer to protect the principal layer from mechanical friction (i.e., wear as it rubs against an internal metal carcass). The metal carcass prevents collapse of the pipe from the sub-sea environment. A sacrificial layer may also be placed outside the principal PA layer to prevent friction wear of the principal layer with outer metal windings used to contain the often high internal pressures of the pipe which can be over 100 atmospheres.

Prior art shows that for PA-11 the measurement of the molecular weight of PA-11 using witness coupons or taking small samples of the PA liner is a means for monitoring aging of the PA liner. Molecular weight and such associated properties as viscosity, retention volume in size exclusion chromatography (SEC), multiangle laser light scattering (MALLS), and osmotic pressure have been shown to be correlated with the PA-11 liner's performance and mechanical properties. See, for example, U.S. Pat. No. 5,614,683 which is herein incorporated by reference.

Recently, we showed that for PA-11, the molecular weight and associated measurement properties such as viscosity decay from their unaged value down to a final equilibrium value. See A. Meyer, N. Jones, Y. Lin, D. Kranbuehl, Macromolecules 35 (7) 2784–2798 (2002). The equilibrium occurs as reported by us due to a recombination reaction competing with the hydrolysis-aging mechanism which lowers the molecular weight. At a certain point in time, these two rates become equal and the molecular weight remains unchanged.

SUMMARY OF THE INVENTION

It is the object of this invention to provide a method to quickly, accurately and far in advance of the replacement time, determine the molecular and performance properties of the final degraded state of a polymer component in the actual use environment. Determining these molecular and performance properties accurately and far in advance of the time for replacement, is the key to cost effective, safe use of polymer structures where falling below specified physical properties can result in catastrophic failure. Periodically monitoring these properties and the potential need for replacement under actual use conditions in the field is obviously critical for establishing the continuing validity of the previous determination and updating or correcting that evaluation. For structures such as offshore pipelines and airplanes where replacement planning must occur far in advance, the key to cost effective safe use is to identify the replacement time far in advance.

A key to establishing the replacement time is determining the final degraded state in a particular use environment long before that state will occur. For many polymers such as PA-11, this means determining the final degraded state's mechanical properties and molecular properties such as the final degraded equilibrium molecular weight. This is shown in the equations used to calculate the change in molecular weight and thereby performance ductility with time. See A. Meyer, N. Jones, Y. Lin, D. Kranbuehl, Macromolecules 35 (7) 2784–2798 (2002). The equilibrium molecular weight or associated quantity such as equilibrium viscosity is the key parameter in the aging equation. Normally, it can only be accurately determined when the polymer is near its end of life and is close to being fully degraded in the actual use environment. Obviously, this is very near, at or after the prudent replacement time. The final degraded state is strongly dependent on the environment such as oil-gas-water, its pH, the temperature, operating pressure, the presence of buffering salts, gases such as oxygen, $CO_2$ and $H_2S$; additives introduced into the environment and other chemicals or mechanical stresses introduced from the environment and/or operating procedures. These factors are interrelated and complex, which makes predictions based on models inaccurate and unreliable. Equally important for some polymers such as PA-11 is the fact that the final degraded state and properties such as the equilibrium molecular weight, which depends on these specific conditions in the field, can be above, near or below the required mechanical and chemical properties where the polymer becomes unacceptable and needs to be replaced. If the final degraded state is above the replacement value, the polymer structure has the potential for a very long extended life based on the physical and/or molecular criteria for replacement. This is because the polymer's properties in its final aged state remain safely above the failure condition. That is the failure condition is never achieved by the aging mechanisms in that particular environment. When the final physical and/or molecular properties are near the prudent required safe use value, or below, the change in these properties needs to be carefully and periodically monitored. Further, the elapsed time until replacement is required is strongly dependent on the relation of the final degraded state's properties to the recommended replacement values. Again, this makes model predictions unreliable and thus in situ coupon analysis is the preferred method. This is demonstrated in the chemical aging results for PA-11 and the mechanical-fatigue aging of polymers such as poly vinyl difluoride (PVDF) and polyethylene (PE and PEX).

In summary for polymer materials and the structures made from polymers, having a method to determine this final degraded state in the actual operating environment whether through in the field measurements or duplication in the laboratory through an accelerated procedure is extremely valuable.

DESCRIPTION OF THE DRAWING FIGURES

Figure 2:
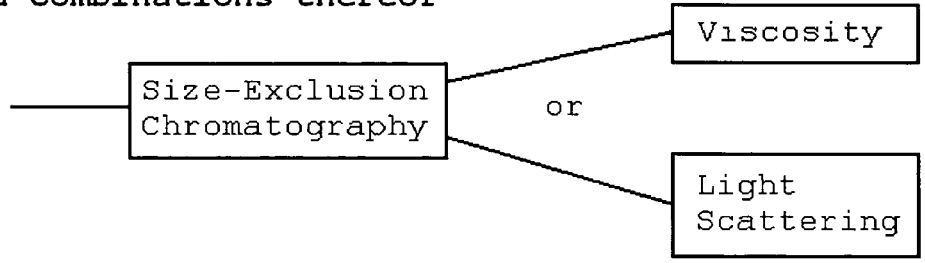

FIG. 1 is a sketch of a section of pipe recovered after many years of use in the field. Coupons cut from this section of retrieved pipe are also shown in the sketch FIG. 2 is a flowchart showing the various instrumental techniques that can be used to measure changes in the molecular weight of a polymer due to chemical aging.

Figure 3:
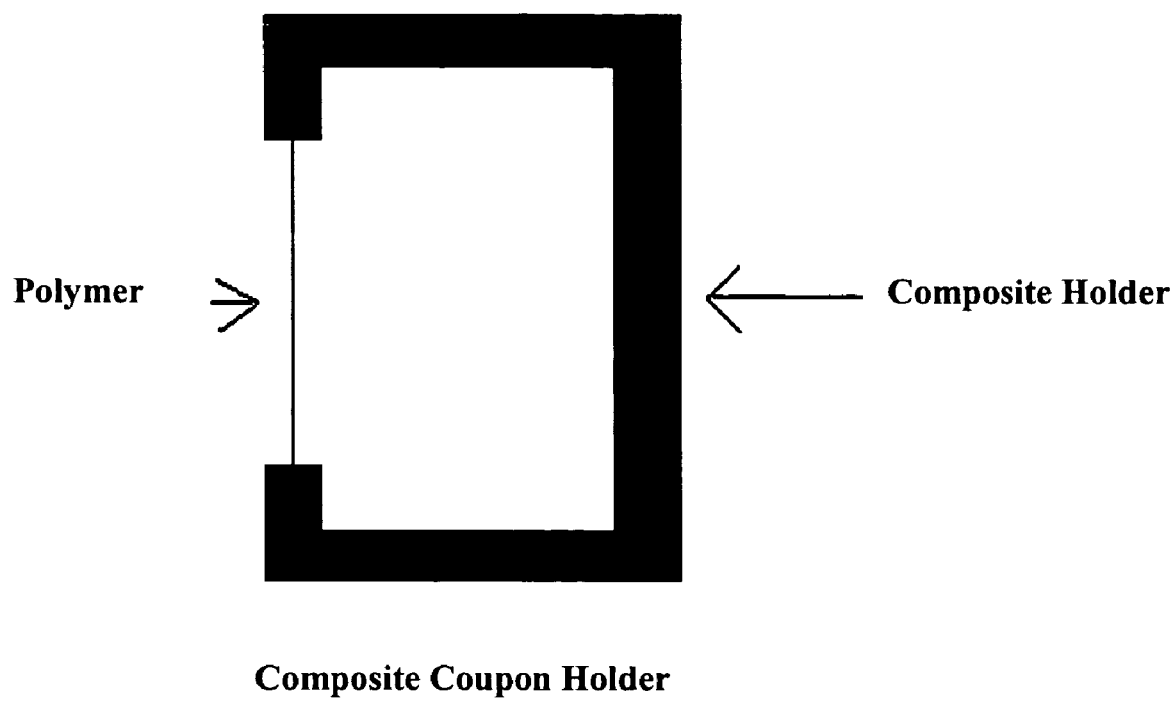

FIG. 3 is a drawing of a coupon holder to monitor physical aging. It is made from combinations of metals and/or polymers such that the thermal expansion-contraction properties of the holder create stress-strain changes in the polymer coupon that duplicates those in the actual structure. A holder which creates a torsion twisting stress-strain variation with temperature is also possible to construct from materials with varying thermal expansion coefficients.

DETAILED DESCRIPTION OF THE PREFERRED EMBODIMENTS OF THE INVENTION

The final degraded state and its mechanical, structural and/or molecular state such as the equilibrium molecular weight or fatigue cycles to failure can be made and monitored by monitoring the change using pre-aged coupons. An example is placing pre-aged coupons such as made from PA, PVDF, PE or PEX in the operating environment such as the oil-gas flow stream inside the pipe during use in the field. The important step here is to use pre aged coupons with molecular and/or physical structural performance properties already pre-aged to a value near the value assigned for safe replacement. By periodically removing pre-aged coupons with physical structural properties and/or molecular properties near the replacement values and measuring their associated experimental characterization quantities such as viscosity, light scattering, chromatography flow volumes, modulus, elasticity or crack growth, which reflect the state of the polymer, it is possible to predict the bounds of the ultimate final degraded state of the structure far in advance. Thereby, it is possible early in the life time of the use to detect the final aged state from the changes in the values of the pre aged coupons put in to the actual operating environment. This is because the witness coupons are already near the final degraded state for the particular use environment. For example, within a rather short period of time, the pre aged PA-11 coupon closest to the final degraded state will remain unchanged with time. The others, depending on how far they are from the final degraded state will continue to change moving toward that value.

If conditions change, periodic monitoring will show that the value of the other various pre aged coupons will also start to change at differing rates, particularly those which previously were stable being closer to the final degraded state for the previous conditions. The change and direction of the change of the other coupons will also be different. Again, pre-aged coupons will change in the direction toward the new value associated with the new field conditions.

In order to create pre aged coupons, in general, the field conditions can be duplicated in the laboratory. In another procedure for acquiring pre aged coupons, it may be possible to create coupons from polymer material taken from pipes or structures which were in use for long periods of time. For oil field applications, the field conditions can be duplicated in the laboratory by recovering production water and crude oil from the flow line, using a pressurizing cell at the operating pressure of the field which is several to 100 bar, using the level of $CO_2$ found in the field, as well as the level of $H_2S$ and any additives used in the flow line. By heating the environment to 20 to 40° C. above the field's operating environment aging will generally occur 4 to 16 times as fast. Thus, in 6 months the state of a pipe after 8 years in service is created. Creating a range of age in the pre aged coupons produces coupons with mechanical-structural and molecular values above, near and even below the recommended replacement values due to aging in that environment. Then these pre-aged coupons which are above or near replacement are thus closer to the field's final degraded state. And these pre aged coupons can be inserted into coupon holders in the field environment, such as in the flow line of a polymer pipe used to transport oil and gas. Thereby, these pre-aged coupons near the predicted final degraded state for that field become very sensitive measures of changes in the final aged performance mechanical and molecular properties for that polymer under those particular conditions. Equally important is how fast and whether the final aged state properties change can be used to quickly detect whether the environment's conditions change.

The method of using pre-aged polymer coupons to determine the replacement time long before chemical aging has brought the polymer structure to that replacement condition can be applied to most polymers and polymer structures which undergo chemical aging such as due to acids, water, oxygen, other chemicals which degrade that particular polymer and high temperature; that is conditions that cause chain scission or changes in the chemical structure of the polymer.

The method of using pre-aged coupons can also be used in physical aging. Here the replacement condition may not be reflected by chemical changes in structure. Rather, it can be stress-strain cycling from external forces and displacements often caused by fluctuations in temperature and pressure. In this case, laboratory or field aged liner, which has been pre-aged through the type of stress-strain cycling of physical aging observed in the field, can be used to create the pre-aged coupon. Here one inserts pre-aged coupons with various degrees of pre-aging stress strain cycling which has brought the coupons near to the replacement criteria property such as tensile, fatigue, strength, modulus, elasticity, crack initiation-propagation or any other physical-mechanical replacement property. By monitoring the elapsed time for these pre-aged coupons with differing mechanical properties or fatigue cycles above or near the replacement criteria to reach the failure-replacement properties while in that field environment, it is possible to construct and predict the time for replacement in that field's actual environment.

EXAMPLE ONE

A new PA-11 liners molecular weight (Mw) is about 60,000. Normally, it takes ten to twenty years to achieve degradation in the Mw of a polyamide pipe liner down to a Mw near 30,000 and with associated mechanical properties approaching replacement.

Sections of PA-11 pipes recovered from a field after varying amounts of use time were used to cut and make the pre-aged coupons as shown in figure one. These were then inserted into the coupon holder in a flow line in another North Sea field. One coupon had a starting pre aged Mw=32,000, the other a Mw=29,900. Examples of measurement techniques to monitor changes in the molecular weight are shown in FIG. 2. Both were retrieved after one year. The first saw its Mw go from 32,000 to 29,000. The second saw its value of Mw=29,900 go to 29,400. The small change of the second and the change of the first within the accuracy are equal to Mw=29,200, This result suggests both were very near the equilibrium value for the PA-11's final state in that field. Further, the final equilibrium Mw value is shown to be about 29,200. Thus, in one year's time the final future state of the PA-11 liner in that field's use environment was determined. Laboratory studies show it will take many years to achieve that value.

Leaving those coupons in and retrieving after another year will either show no change in Mw indicating no change in the environment or a decrease in both coupons values to a new value indicating a more degradative environment. Neither event could be accurately determined using unaged coupons and retrieving them after the $1^{st}$ or $2^{nd}$ years. This example involves chemical aging due to the acidic water environment. This example would also pertain to radiation aging such as visible, ultra violet or X-rays as examples or thermal aging.

EXAMPLE TWO

Coupons were pre aged at 120° C. in a laboratory pressure cell filled with oil-water taken from the offshore pipeline and with a $CO_2$ pressure duplicating that in the offshore pipeline. After 4 months, the Mw dropped to values near 33,000 representing many years of aging under field conditions.

These pre aged coupons were inserted into similar pressure cells duplicating the 80° and 90° conditions in the Australian field. Again after 6 months all the coupons attained the same Mw, which was above the replacement criteria. Thereby the final Mw for that pipeline was quickly determined which demonstrated long term safe operation in that field's simulated environment.

Putting these coupons into the offshore coupon hold and retrieval after one year, as in example one, will further verify this result and many years in advance. This example would also pertain to radiation aging such as visible, ultra violet or X-rays as examples or thermal aging.

EXAMPLE THREE

Physical aging can be similarly accelerated. Taking bars of the polymer, some with a defined initiation scratch and others without, both types of bars can go through many stress strain cycles approaching the number needed for crack growth, failure or crack initiation in those bars without an initiation scratch.

These pre-fatigued bars are put in an in situ mechanical coupon holder such as shown in FIG. 3 which duplicates in the polymer coupon the stress-strain cycling that occurs in the actual structure. The holder is inserted in to the flow line where thereby the coupons are exposed to the stress-strain cycling due to the temperature, pressure and wave movements over time in the field. Thereby the number of months of exposure until failure and/or crack initiation can be determined quickly under the field conditions by simply examining the time it took in the field to induce failure and relating it to the extent of pre aged fatigue cycling.

FLOW CHART FOR ANALYSIS

Step one: Acquire or generate a pre-aged coupons which have seen an aging environment similar to that in the field.

Step two: Place the pre-aged coupons into a coupon holder which results in additional aging in the field during use similar to that experienced by the material in the structure.

Step three: Remove coupons periodically and evaluate the changes in their performance, physical and/or molecular properties.

Step four: Relate change in properties to time in the field and compare to previous knowledge of laboratory aging studies or knowledge acquired from previous field experience to determine an estimated time for replacement and the anticipated future state of the material versus time.

The invention claimed is:

1. A method for assessing the life expectancy of a polymer lined pipe which transports fluids, comprising the steps of:
   positioning pre-aged polymer witness coupons in said polymer lined pipe, each of said pre-aged polymer witness coupons being made of the same material as a polymer in said polymer lined pipe, and each having a molecular weight, which can be the same or different for each pre-aged polymer witness coupon, which is less than an initial value for said polymer in said polymer lined pipe and more than a threshold replacement value for said polymer in said polymer lined pipe;
   determining an equilibrium molecular weight for said polymer based on changes in the molecular weight of said pre-aged polymer witness coupons over time; and
   comparing the equilibrium molecular weight to said threshold replacement value, and, based on the comparison determining whether
   (i) said polymer lined pipe will need to be replaced, or
   (ii) when said polymer lined pipe will need to be replaced.

2. The method of claim 1 wherein said polymer is selected from the group consisting of polyamides, polyethylenes, and polyvinylfluorides.

3. The method of claim 1 wherein said polymer is polyamide-11.

4. The method of claim 1 wherein said polymer is polyethylene or cross-linked polyethylene.

5. The method of claim 1 wherein said polymer is polyvinyldifluoride.

6. The method of claim 1 further comprising the step of determining a rate of degradation of said polymer based on said comparing step.

7. The method of claim 1 wherein said fluids include a water-gas-oil mixture.

8. The method of claim 1 further comprising the step of obtaining said pre-aged coupons from a polymer lined pipe which has been in service for a known period of time.

9. The method of claim 1 further comprising the step of aging coupons in a laboratory under conditions which simulate an in-use environment to obtain pre-aged coupons.

10. A method of monitoring and controlling degradation of a polymer lined pipe which transports fluids, comprising the steps of:
    positioning pre-aged polymer witness coupons in said polymer lined pipe, each of said pre-aged polymer witness coupons being made of the same material as a polymer in said polymer lined pipe, and each having a molecular weight, which can be the same or different for each pre-aged polymer witness coupon, which is less than an initial value for said polymer in said polymer lined pipe and more than a threshold replacement value for said polymer in said polymer lined pipe;

determining a rate of degradation of said polymer based on a rate of change in molecular weight of said pre-aged polymer witness coupons over time; and adjusting a pumping rate and/or composition of said fluids in said polymer lined pipe based on said rate of degradation determined in said determining step.

11. The method of claim 10 further comprising the step of increasing the pumping rate or changing the composition of said fluids if the rate of degradation is less than a selected value.

12. The method of claim 10 further comprising the step of increasing the pumping rate or changing the composition of said fluids if the rate of degradation is less than a selected value.

13. The method of claim 10 wherein said polymer is selected from the group consisting of polyamides, polyethylenes, and polyvinylfluorides.

14. The method of claim 10 wherein said polymer ispolyamide-11.

15. A method for monitoring degradation of a polymer material, comprising the steps of:

positioning pre-aged polymer witness coupons in a same environment in which a component comprising said polymer is used, each of said pre-aged polymer witness coupons being made of the same material as a polymer in said component, and each having a molecular weight, which can be the same or different for each pre-aged polymer witness coupon, which is less than an initial value for said polymer in said component and more than a threshold replacement value for said polymer in said component;

determining an equilibrium molecular weight for said polymer based on changes in the molecular weight of said pre-aged polymer witness coupons over time; and comparing the equilibrium molecular weight to said threshold replacement value, and, based on the comparison determining an amount of degradation of said polymer.

16. The method of claim 15 wherein said amount of degradation is due to chemical degradation.

17. The method of claim 15 wherein said amount of degradation is due to thermal degradation.

18. The method of claim 15 wherein said amount of degradation is to radiant energy degradation.

19. An array of polymer witness coupons for assessing the life expectancy of a polymer lined pipe which transports fluids, comprising:

at least two pre-aged polymer witness coupons, each of said pre-aged polymer witness coupons being made of the same material as a polymer in said polymer lined pipe, and each having a molecular weight, which can be the same or different for each pre-aged polymer witness coupons, which is less than an initial value for said polymer in said polymer lined pipe and more than a threshold replacement value for said polymer in said polymer lined pipe; and means for positioning said at least two polymer witness coupons in said polymer lined pipe such that the at least two polymer witness coupons are exposed to the same environment conditions of said polymer in said polymer lined pipe.

20. The array of claim 19 wherein said polymer is selected from the group consisting of polyamides, polyethylenes, and polyvinylfluorides.

21. The array of claim 19 wherein said polymer is polyamide-11.

22. A system for assessing the life expectancy of a polymer lined pipe which transports fluids, comprising:

an array of pre-aged polymer witness coupons, each of said pre-aged polymer witness coupons being made of the same material as a polymer in said polymer lined pipe, and each having a molecular weight, which can be the same or different for each pre-aged polymer witness coupon, which is less than an initial value for said polymer in said polymer lined pipe and more than a threshold replacement value for said polymer in said polymer lined pipe, and each of said pre-aged polymer witness coupons being positionable in and retrievable from a position where said pre-aged polymer witness coupons are exposed to the same environmental conditions of said polymer in said polymer lined pipe;

means for determining an equilibrium molecular weight for said polymer based on changes in the molecular weight of said pre-aged polymer witness coupons over time; and means for comparing the equilibrium molecular weight to said threshold replacement value, and, based on the comparison determining whether
 (i) said polymer lined pipe will need to be replaced, or
 (ii) when said polymer lined pipe will need to be replaced.

* * * * *